(12) United States Patent
Forsythe et al.

(10) Patent No.: US 6,322,002 B1
(45) Date of Patent: Nov. 27, 2001

(54) AEROSOL GENERATING DEVICE

(75) Inventors: Darol Forsythe, Boise; John Forsythe, Nampa, both of ID (US); Joel Micka, Kennewick, WA (US)

(73) Assignee: Pin/Nip, Inc., Meridian, ID (US)

( * ) Notice: Subject to any disclaimer, the term of this patent is extended or adjusted under 35 U.S.C. 154(b) by 0 days.

(21) Appl. No.: 09/372,398

(22) Filed: Aug. 10, 1999

Related U.S. Application Data

(63) Continuation-in-part of application No. 08/777,915, filed on Dec. 23, 1996, now Pat. No. 5,935,660, which is a continuation-in-part of application No. 09/358,949, filed on Jul. 22, 1999.
(60) Provisional application No. 60/009,451, filed on Dec. 29, 1995.

(51) Int. Cl.$^7$ .............. B05B 1/24; B05C 1/00; F23D 11/16; F23D 11/40; F23D 14/62
(52) U.S. Cl. .............. 239/135; 239/419; 239/423
(58) Field of Search ............ 239/419, 423, 239/135, 427.3, 427.5, 419.3; 118/715, 300, 24, 13, 21; 427/446; 126/59.5

(56) References Cited

U.S. PATENT DOCUMENTS 3,770,048 * 11/1973 Linhardt et al. .............. 165/1
4,133,485 * 1/1979 Bouvin .............. 239/399
4,669,658 * 6/1987 Nevgod et al. .............. 239/423

* cited by examiner

Primary Examiner—David A. Scherbel
Assistant Examiner—Davis Hwu
(74) Attorney, Agent, or Firm—TraskBritt

(57) ABSTRACT

An improved combustion-type fogging apparatus and process for applying herbicides, insecticides and the like, as an aerosol is disclosed herein. The apparatus includes an improved combustion chamber with counter-current flow of combustion and supplemental air along with a stator at the downstream portion of the combustion chamber. The combustion chamber also has a hydrocarbon fuel burner to produce hot gases which along with the combustion air and supplemental air forms a hot gas flow into an aerosol chamber wherein a liquid or molten material is introduced for the purpose of being converted into a stable aerosol or fog for introduction into a storage facility or for other purposes of applying an aerosol of an insecticide, herbicide or other liquid or molten material.

8 Claims, 7 Drawing Sheets

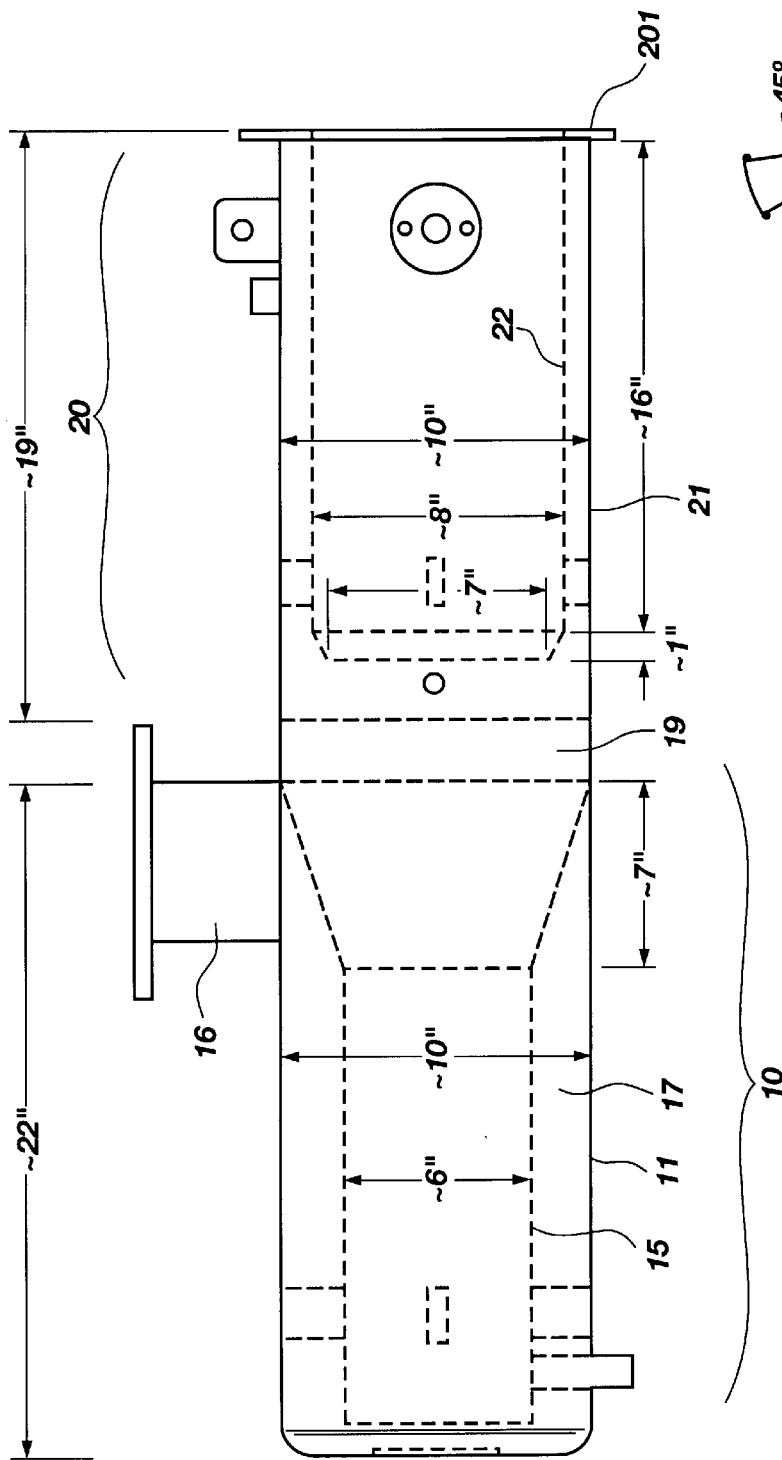
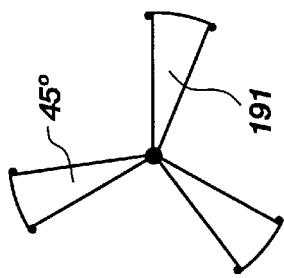
Fig. 6
Fig. 7

AEROSOL GENERATING DEVICE

CROSS REFERENCE TO RELATED APPLICATION

This application is a continuation-in-part of application Ser. No. 08/777,915, filed Dec. 23, 1996, now U.S. Pat. No. 5,935,660, issued Aug. 10, 1999, which application claims the benefit of U.S. Provisional Application No. 60/009,451, filed Dec. 29, 1995. U.S. Pat. application Ser. No. 09/358,949, filed Jul. 22, 1999, is a continuation-in-part to said Ser. No. 08/777,915, and is also related. The specification of each of these related applications is hereby incorporated by reference.

BACKGROUND OF THE INVENTION

1. Field of the Invention

This invention relates generally to devices for forming aerosols and especially to thermal combustion aerosol devices, also known as foggers.

2. State of the Art

It is known in the art to apply sprout inhibitors of various types to potatoes to prevent sprouting during storage. One of the earlier patents relating to this is the Plant patent, U.S. Pat. No. 3,128,170, related to a method for applying isopropyl-N-chlorophenylcarbamate (CIPC) to a potato storage facility. As noted in the Plant patent, CIPC is a solid at room temperature which is generally dissolved in polar solvents such as propylene glycol and, more recently, methanol. A typical weight of CIPC in solution is about 78% of the weight of the solution for commercial products using methanol as the solvent. A solution of CIPC has generally been desirable for forming aerosols of CIPC as well as for handling.

More recent patents relating to the application of CIPC to a storage facility are Sheldon and Morgan, respectively, U.S. Pat. Nos. 4,226,179 and 4,887,525. Sheldon involves a process for ultrasonically vaporizing a solution of CIPC, while the Morgan patent relates to an improved technique for moderating the air flow within a storage facility to get better distribution of CIPC aerosol produced from solvent-based system.

Sheldon refers to the possibility of applying non-solvent based CIPC. No example of such technique is given in Sheldon nor is there any suggestion as to how such a technique would be accomplished. Sheldon indicates that a solvent may be necessary in order to keep the chemical liquid in the spray nozzle.

Sheldon notes that thermal fogging tends to produce large droplets of CIPC, cause degradation of the CIPC and warm the stored potatoes, which may promote bacteria growth. Thus, Sheldon was directed to a non-thermal or low-thermal application in contrast to the thermal fogging apparatus in common use.

The technique utilized in the Morgan patent involved thermal fogging prior to introduction of the fog of CIPC in the circulating air stream of a storage facility. Thermal foggers which have been commercially used are constructed similar to that illustrated in FIG. 12, wherein a propane flame burns within a hollow pipe (combustion chamber) which is enclosed by another generally cylindrical enclosure. It is into this outer enclosure that the solvent based CIPC is introduced. The solvent based CIPC is frequently introduced near the distal end of the combustion chamber with the solvent solution of CIPC being blended with the combustion gases emanating from the combustion chamber. This results in the solvent generally being evaporated and the CIPC being converted into a mixture of vapor (gas) and particles of CIPC, both liquid and solid particles.

The products of combustion exiting the combustion chamber are generally oxygen poor, so much of the methanol solvent is not burned. Thus, it evaporates and often decomposes to formaldehyde and formic acid, both of which are toxic. The products of combustion form a reducing atmosphere in a storage facility and further create an over pressure from the large volume of gases entering the facility. The reducing atmosphere causes the potatoes to be stressed, resulting in some of the starch being converted to sugars. Potatoes having a high sugar content yield french fries which are dark brown in color when cooked, especially at the tips of the french fries. This is generally undesirable and reduces the value of such stored potatoes. An over pressure results in much of the treatment chemical being vented from the storage facility.

As the Morgan patent noted, one of the problems had been that the CIPC tended to collect on the fans of the air circulation system of the storage facility as well as on the vent pipes and other portions of the facility. CIPC is not really effective for treating potatoes unless it is in contact with the potatoes, that is, deposited directly on the potatoes. The prior art thermal fogging system introduces into the potato storage facility all the products of combustion of the propane gas burner as well as evaporated methanol, or such other solvent, including decomposition products of methanol such as formaldehyde, formic acid and the like. Given that storage facilities are maintained at relatively low temperatures, in the neighborhood of about 40 to 50° F., these products, methanol, formic acid, formaldehyde, and the like, can liquify (condense) within the facility and can also be deposited on the potatoes. Since this can happen, it can also create a vapor pressure of these products within the storage facility long after a sprout inhibition treatment has occurred. Thus, a facility can be rendered unsafe for personnel to work in for quite some time. Although thermal fogging with thermal foggers of the type illustrated in FIG. 12 has been done for a long time, and storage sheds so treated have been relatively free of sprout growth, nevertheless the method is inefficient in its application of CIPC, i.e., CIPC decomposes to some extent, contaminates the storage facility with toxic, undesirable material, and is lost by venting.

Both Sheldon and Morgan involve methods and apparatus which introduce large volumes of gases, air or combustion products into a storage facility. This creates an over pressure within the facility and causes venting and loss of CIPC from the facility.

The technique of forming aerosols, i.e., a stable fog, of herbicides, pesticides, etc. has conventionally involved the use of solvents or carriers. In U.S. Pat. No. 2,460,792 of Pabst et al., the technique of adding a mixture of oils to obtain a stable aerosol is disclosed. A principal reason for the use of solvents with CIPC and similar sprout inhibitors apparently has been to accommodate the application of the sprout inhibitor as an aerosol and to facilitate handling of liquids by applicators.

While the Sheldon patent suggests the forming of a liquid particle "fog" by ultrasonic means, the technique has apparently not been practiced commercially and the patent is devoid of any instruction as how this is done from a non-solvent system. Current field techniques for commercial application of CIPC has been by fogging of a solvent solution of CIPC via a thermal fogger of the prior art type, frequently using moderated fan speed as taught by the Morgan patent.

While effort has been expended towards improving the materials to be converted to an aerosol, little effort has heretofore been made to improve the thermal fogging apparatus to be more efficient.

SUMMARY OF THE INVENTION

A combustion-type thermal fogger having improved construction and operation has been invented. The fogger, also identified herein as an aerosol generating device, can be used to make stable aerosols from a variety of liquid materials, including molten materials such as molten CIPC. It is, however, equally useful for materials which are liquid at room temperature. The efficiency of the fogger is such that stable fogs can be formed at relatively low temperatures, e.g., as low as about 400° F., for molten CIPC and even lower for materials which are liquid at room temperature as materials dissolved in solvents whereby the solvent is liquid at room temperature.

The fogger has an outer barrel which serves to house and support the entire structure. The outer barrel is cylindrical in shape and constructed of metal, typically, mold steel. Internally, the interior space comprises a combustion chamber, a vaned stator assembly and an aerosol formation chamber. The outer barrel is preferably formed as two separate barrels, one for the combustion portion or zone of the device and the other for the aerosol formation portion or zone.

The combustion chamber is situated within an inner barrel (cylinder) which is generally concentric within said outer barrel and is smaller in diameter than the outer barrel. Flame from a hydrocarbon burner extends into the combustion chamber formed by the inner barrel. Combustion air is introduced into the annular space between the outer and inner barrels and preferably moves counter-currently to the combustion gases in the combustion chamber to flow downward into the rear of the combustion chamber to mix with the hydrocarbon fuel, typically, in a gaseous form at the point in the fogger. The annular space is sealed from the flame arrestor section and aerosol formation section. The inner barrel is spaced from the rear of the device so the hot air is forced to flow into the combustion chamber. The introduction of the fresh air into the annual space further serves to keep the outer barrel relatively cool.

The mix of combustion gases and excess air (hot air) at a temperature of above about 400° F., generally, and typically at about 500° F. and above, flows from the combustion chamber into the aerosol formation section (chamber) after passing through a stator vane assembly which can act as a flame arrestor. The stator vane assembly principally acts to cause turbulent flow to occur in the aerosol formation chamber which assists in getting a stable aerosol of small particles.

The aerosol formation chamber or section has an inner cylindrical barrel, also, which is substantially concentric with an outer cylindrical barrel. The inner cylindrical barrel permits hot gases and air to pass along the exterior of the inner cylinder and, ultimately, to mix with the aerosol just as the aerosol is discharged from the fogger.

Most of the hot gases and air leaving the combustion chamber and entering the aerosol forming chamber are directed through the interior of the inner cylindrical barrel in the aerosol forming zone. The liquid material to be fogged is introduced into the interior of the inner aerosol cylindrical barrel of the aerosol formation zone.

Most liquid materials to be fogged are flammable, thus, it is undesirable for the flame from the combustion chamber to enter the aerosol formation zone. The length of the combustion chamber and the stator vane assembly acting as a flame arrestor preclude this from occurring. The stator vane assembly is typically beyond the usual length of the flame in the combustion zone.

In the aerosol formation zone the liquid material to be fogged is introduced in one of several ways. The liquid material, such as a hot molten material or a material which is liquid at room temperature, is injected directly into the hot gas stream from an inspection tube or it may be directed onto an impact plate positioned in the hot gas stream. The liquid can be introduced at either low or high pressure and is preferably introduced through a nozzle assisted by high pressure air and directed counter-currently into the hot gas stream.

BRIEF DESCRIPTION OF THE SEVERAL VIEWS OF THE DRAWING

FIG. 6 is an elevational sectional view of a combustion fogging device of the instant invention;

FIG. 7 is an elevational view of a stator vane assembly utilized in the combustion fogging device of the instant assembly;

DETAILED DESCRIPTION OF THE INVENTION

Further description of the invention may be facilitated by reference to the attached drawings.

Figure 1:
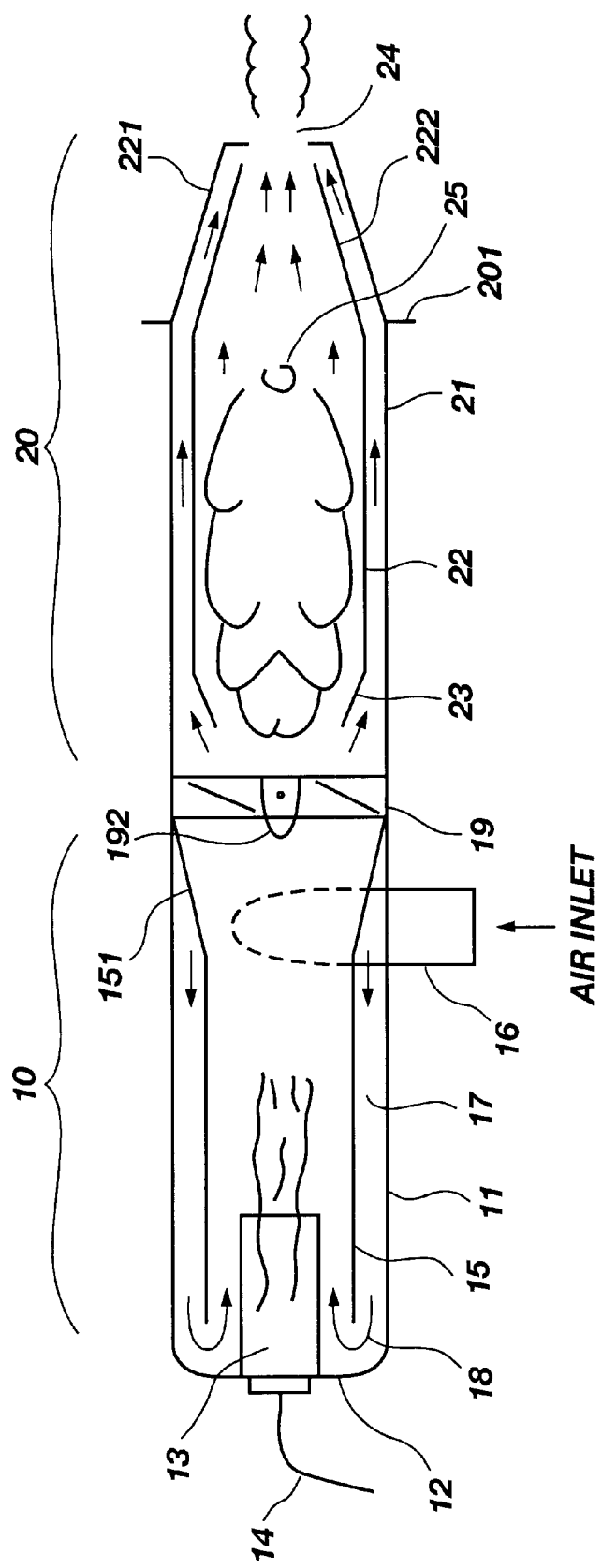
FIG. 1 is a schematic elevational sectional view of a combustion thermal fogger of the instant invention.

FIG. 1 is a schematic sketch of a combustion fogging apparatus having a combustion zone (section), a stator (flame arrestor) and an aerosol formation zone (section).

The combustion zone 10 is formed by a large pipe (barrel) cylindrical in nature 11 having a diameter anywhere from about 6 to 12 inches as an outside shell with a substantially closed end 12 having a port for insertion of a burner 13 having a fuel line 14. An inner cylindrical member 15 substantially concentric with cylindrical member 11 is positioned inside of the cylindrical member 11 and air inlet pipe 16 introduces air into the annular space 17 formed between the inner cylindrical member 15 and the outer shell or cylindrical member 11. The air inlet is preferably very close to the downstream terminus of the combustion zone 10 so that air introduced into the annulus 17 flows counter-current to the hot combustion gases and flame produced by the burner 13. The inlet air is heated in the annulus 17 as it flows counter-currently which assists in keeping the outer shell cylindrical member 11 cooler than it would otherwise be and it also causes inlet air to increase in temperature so when the air turns the corner at position 18 to be introduced into the inside of the inner member 15, i.e., combustion chamber, to mix with the fuel and to provide the sole combustion air or to provide supplemental combustion air, that the air is already heated and, therefore, causes a more efficient flame and a more efficient hot combustion gas mixture to be formed.

The inner pipe or cylindrical member 15 is flared to form a cone at its downstream section in the combustion zone so that the air introduced through inlet 16 must flow counter-currently. The cone base is sealed to the outer barrel 11 adjacent the terminus of the combustion zone. It is at this point that a stator vane assembly 19 is positioned to act potentially as a flame arrestor and to cause the air and combustion gases to flow in a turbulent manner into the aerosol-forming zone.

Typically, the vanes of the stator vane assembly 19, as illustrated in other drawings attached hereto, are set at an angle to the combustion gas flow exiting the combustion zone to provide efficient flame arresting characteristics in case of abnormal operation. This angular positioning of the vanes generally will cause the combustion gases exiting the combustion zone to flow in turbulent manner into the aerosol formation zone 20.

It should be understood that the fogging or aerosol apparatus of FIG. 1 may be efficiently used without a stator vane assembly 19 although it may require additional length to the total apparatus so that the aerosol formation zone 20 is more remote from the combustion zone 10 so that the flame in the combustion zone will not reach any of the liquid material introduced in the aerosol formation zone 20 since most liquid materials, whether a liquid at room temperature or whether molten at room temperature, are combustible. Thus, a stator vane assembly with angled blades is generally preferred.

In many prior art combustion aerosol devices, it is not unusual when operating at high capacities with increased fuel and an increased flame length to cause occasionally the flame to contact the aerosol-formed material and cause a flame to exit the combustion aerosol apparatus therefor making it useless and requiring that the whole apparatus be rapidly shut down to prevent damage to the apparatus and to prevent an explosive situation from occurring. The presence of a stator vane assembly 19 significantly reduces the likelihood of flame from the combustion zone even under abnormal operation reaching any of the combustible material introduced in the aerosol formation zone 20.

The aerosol formation zone 20 is constructed of an outer pipe or barrel 21 and an inner pipe or barrel 22 with an annular space formed between the two. Preferably, at the inlet end of the inner barrel 22, a short conical section 23 reduces the diameter in the direction of the combustion zone 10 so that a significant amount of the combustion gases and supplemental hot air exiting the combustion zone bypass the aerosol formation chamber within the inner barrel 22. This annular space is referred to herein as the hot air bypass space although it does contain combustion gases as well and it recombines with the aerosol-formed material as the aerosol material exits the aerosol formation chamber. The aerosol exits at port 24 and is a mixture of the bypassed hot air and combustion gases and the aerosol in form of very fine droplets and combustion gases which pass through the inner barrel 22. The aerosol-forming material, that is, a liquid material, is introduced through port 25.

Figure 2:
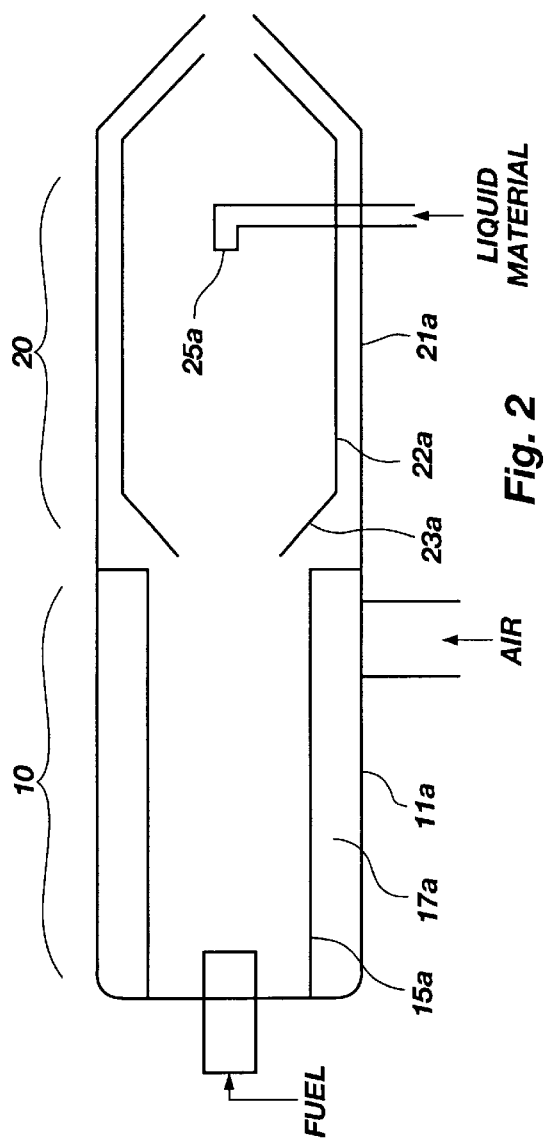
FIG. 2 is a schematic elevational sectional view of a combustion thermal fogger having a different construction than that illustrated in FIG. 1.
Figure 3:
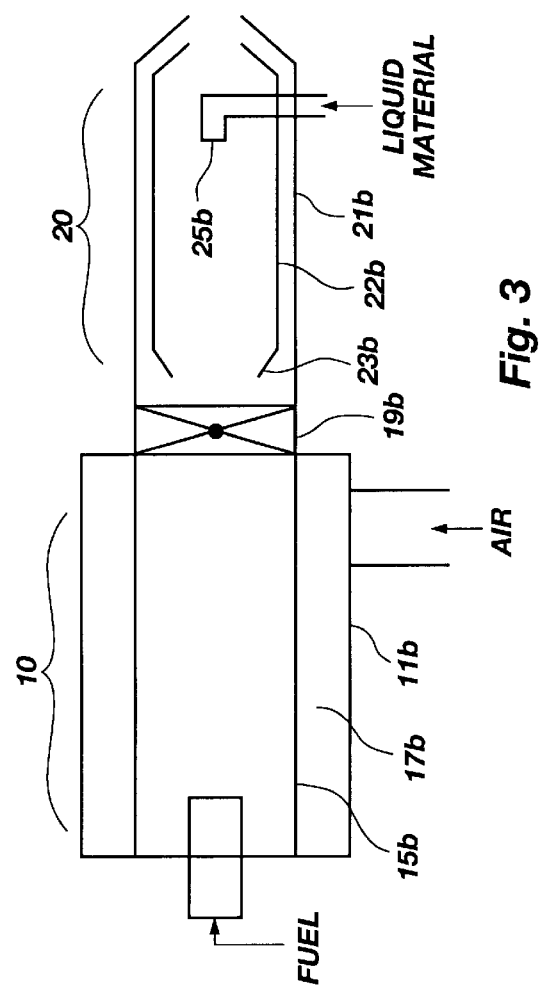
FIG. 3 is a schematic elevational sectional view of a combustion thermal fogger having a different construction than that illustrated in FIG. 1.

An alternative fogging apparatus is illustrated in FIG. 2 wherein the combustion zone 10 is formed of an outer shell which an inner shell is positioned substantially concentrically to the shells being concentric with a hot air zone 17a being formed between the inner shell and the outer shell to provide air to the fuel for formation of a flame and to provide hot combustion gases. In FIG. 2, the outer shell 11a has the same diameter as the aerosol formation zone shell 21a while the inner shell 15a has a smaller diameter than the inner shell 22a of the aerosol formation zone 20. Also, in FIG. 2 there is no stator vane assembly 19 as illustrated in FIG. 1 which generally would require that the liquid material inlet 25a be positioned slightly farther from the terminus of the combustion zone 10 than would be necessary in a structure such as FIG. 1 or FIG. 3. In the device of FIG. 2, it is generally preferred that a stator vane assembly be utilized for the purpose of introducing the combustion gas/air flow into the aerosol forming chamber in a turbulent manner. The assembly of FIG. 3 is such that the inner cylinder 15a and the combustion zone 10 is the same diameter as the outer cylinder 51b and 21b so that the inner cylinder 22b in the aerosol formation zone 20 is of a narrower diameter than the inner cylinder 15 in FIG. 1. A stator vane assembly 19b is present in the device of FIG. 3. In both FIGS. 2 and 3, the inlet air passes through into the annular zone 17 and flows in a counter-current manner as is preferred in the instant invention.

Figure 4:
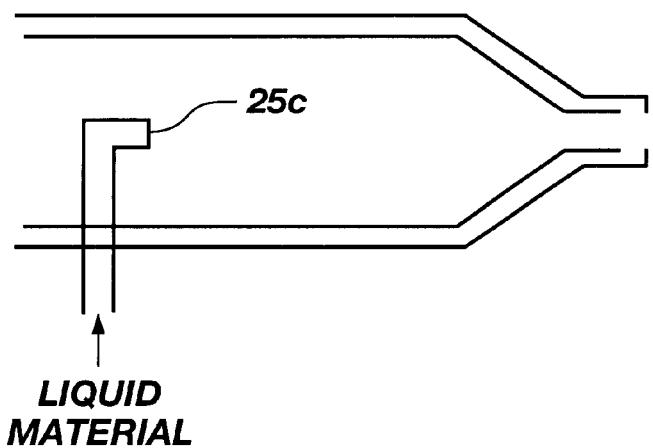
FIG. 4 is a schematic elevational view showing a different position and manner for introducing a liquid material to be fogged.
Figure 5:
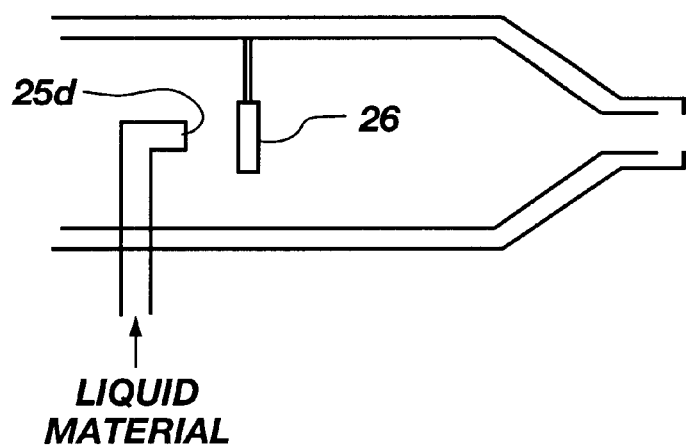
FIG. 5 is a schematic elevational view showing a different position and manner for introducing a liquid material to be fogged.

In FIGS. 4 and 5, a slightly different arrangement for the liquid material insert is shown wherein the inlet port 25c in FIG. 4 and 25d in FIG. 5 are positioned closer to the combustion zone and inject the liquid material into the combustion gases concurrently with the flow of the combustion gases while in FIGS. 1, 2 and 3, the liquid material is introduced into the combustion gases in a counter-current fashion and, preferably, in FIGS. 1, 2 and 3, a nozzle is utilized whereby the liquid material is dispersed into droplets by the nozzle. In FIG. 5, the liquid material may be introduced as a jet of liquid material that strikes a dispersion plate 26 to disperse the jet or stream of liquid material into droplets so that it forms an aerosol within the aerosol formation zone. In FIGS. 4 and 5, it is generally preferred that a stator vane assembly be used between the combustion zone and the aerosol formation zone.

FIG. 6 is a elevational view of the device of the instant invention in which the combustion zone 10 is similar to that illustrated in FIG. 1; however, dimensions are illustrated of an approximate nature on FIG. 6. The dimensions of the aerosol formation zone 20 are also illustrated. These dimensions are for illustrative purposes and provide general ratios inasmuch as the dimensions may be altered without significant impact on the operation of the apparatus, especially if the dimensions are reduced or increased proportionately. The length of the combustion zone from its plate having the burner port to the stator vane assembly 19 is approximately 22 inches with the stator vane assembly 19 having a width of approximately 2 inches while the aerosol formation zone 20 form the stator vanes to the end of its zone is approximately 19 inches.

A cone assembly (not shown) is fitted to the discharge end of the aerosol formation zone 20. This cone has general shape illustrated in FIG. 1 and is identified in FIG. 1 as items 221 and 222. This cone, as illustrated in FIG. 1, generally has a length from flange 201 to the discharge port 24 of about 8 to 12 inches. The inner cylinder 15 in the combustion zone has a diameter of about 6 inches while the outer shell 11 has a diameter of about 10 inches and the inlet pipe 16 for the inlet air has an inner diameter of approximately 7½ inches, thus otherwise indicated generally diameters are inner diameters. The aerosol formation zone 20 has an inner diameter of about 10 inches for its outer shell 21, while the inner shell 22 has a diameter of about 8 inches. Inner shell 22 from flange 201 to its terminus close to the stator is approximately 17 inches, thus there is a space between the stator and the inner shell of about 2 inches.

The port 251, illustrated in FIG. 6, is the introductory port to the nozzle or inlet for the liquid material 25. In the event that a stator is not used, then the position of this inlet port from the terminus of the combustion zone 10 must be at an increased distance in comparison to an apparatus in which a stator is utilized. This increase in distance may be anywhere from about approximately 9 inches to about 18 inches, depending upon the diameter and the flow through volume per unit time of the combustion gases. Thus, the presence of a stator, as illustrated in FIG. 7, in addition to other advantages, has the characteristic of reducing the overall length of the aerosol formation chamber by a distance of up to about 25% to about 50%.

Although the inner barrels in both the combustion zone and the aerosol formation zone are shown as having tapered ends, this construction, while generally preferred, may be altered, provided that the majority of the hot gases and hot air exiting the combustion zone flow through the aerosol formation chamber with a minor amount of said hot gases and hot air flowing into the annual space between the inner and outer barrels of the aerosol formation zone.

Figure 8:
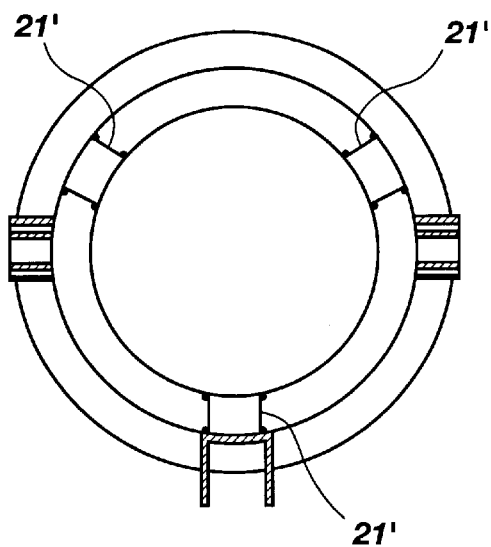
FIG. 8 is an elevational view of the aerosol formation zone of a device of the instant invention.

In FIG. 8, a cross-sectional view of the aerosol formation zone is illustrated showing three supports 211 positioning the inner barrel in a spaced, concentric position with respect to the outer barrel.

Figure 9:
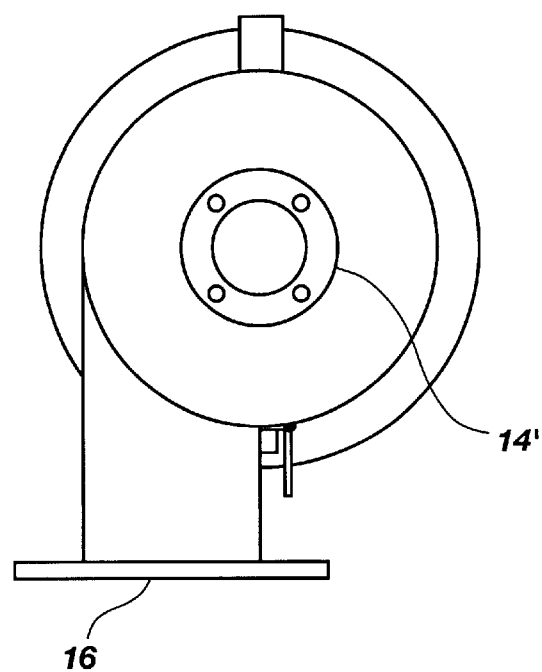
FIG. 9 is an elevational rear view of the combustion zone.

In FIG. 9, a rear, elevational view of the combustion zone is illustrated showing inlet air pipe 16 positioned to introduce the inlet air tangentially into the annual space between the concentric barrels of the combustion zone. Burner flange 141 is illustrated as an attachment means for the burner assembly (not shown).

Various liquid herbicides, pesticides and the like are liquid at room temperature or are dissolved in solvents so that the solution is liquid at room temperature. All such liquids may be utilized effectively in the device of the instant invention, including liquid sprout inhibitors for potatoes such as 1,4 Dimethyl naphthalene and other alkyl isomers of naphthalene useful as herbicides, pesticides, etc. which are liquid at room temperature.

The instant invention is unique in various respects, especially in its use of:

1) a stator assembly separating the combustion chamber from the aerosol formation chamber, said stator assembly performing several functions, namely, to act as a flame arrestor under unusual operating conditions and to interrupt the typically laminar flow of combustion gases and additional hot air to create turbulent flow in the aerosol formation chamber;

2) complete counter-current flow of air introduced in the combustion zone annulus which creates more efficient combustion and a more uniform temperature within the combustion chamber, i.e., within the inner barrel;

3) a conical flaring of the inner barrel in the combustion zone adjacent the stator assembly. In the combustion chamber the burning fuel forms a large quantity of combustion gases. Thus, the quantity of gas flowing downstream of the burner is much greater than the gas flow adjacent the burner. The flaring of the combustion chamber inner barrel accommodates the increasing gas volume and directs it over and through the complete diameter of the stator assembly; and 4) positioning of the inner barrel in the areas of formation zone with its upstream end proximate the stator assembly.

The device of the instant invention may be utilized with any type of liquid fuel, e.g., molten, CIPC or other molten liquid, may be utilized through various introduction means to introduce the molten liquid into the aerosol formation chamber.

Although it is desirable to utilize a dual concentric barrel arrangement in the aerosol formation zone so that the inner barrel forms the aerosol formation chamber, a single barrel arrangement may be utilized because of the turbulent gas flow which tends to keep the whole chamber hot, especially if insulation is used on the exterior of the barrel, as is desirable for even a dual barrel aerosol formation zone.

The flow of hot gas about the extended surface of an inner barrel keeps the inner barrel hot and prevents deposits of solid material forming there when a material is fogged which is typically solid at room temperature or temperatures significantly above room temperature, e.g., CIPC, whether said CIPC is introduced as a molten material or dissolved in a solvent. This would also be true of some forms or isomers of substituted naphthalenes which are solid at room temperature.

Materials which are liquids at room temperature are readily processed in the device of the instant invention to form stable aerosols (fogs) utilizing various liquid introduction means such as spraying the liquid against a plate within the aerosol formation chamber or directing the liquid through an atomization nozzle either with or without the use of high pressure air in the nozzle.

Figure 10:
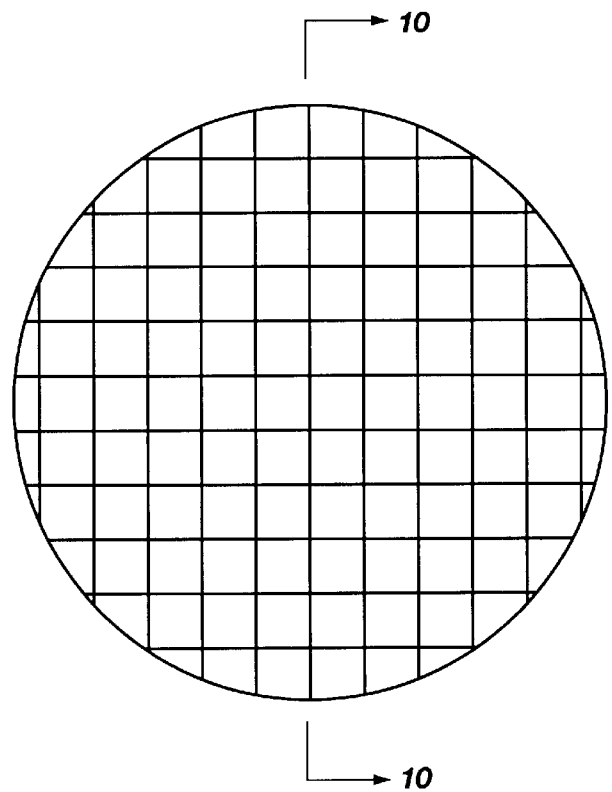
FIG. 10 is an elevational view of a grid-like stator assembly.
Figure 11:
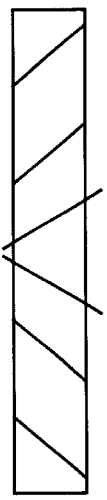
FIG. 11 is a cross-sectional view of the stator of FIG. 10 along section lines 10—10.
Figure 12:
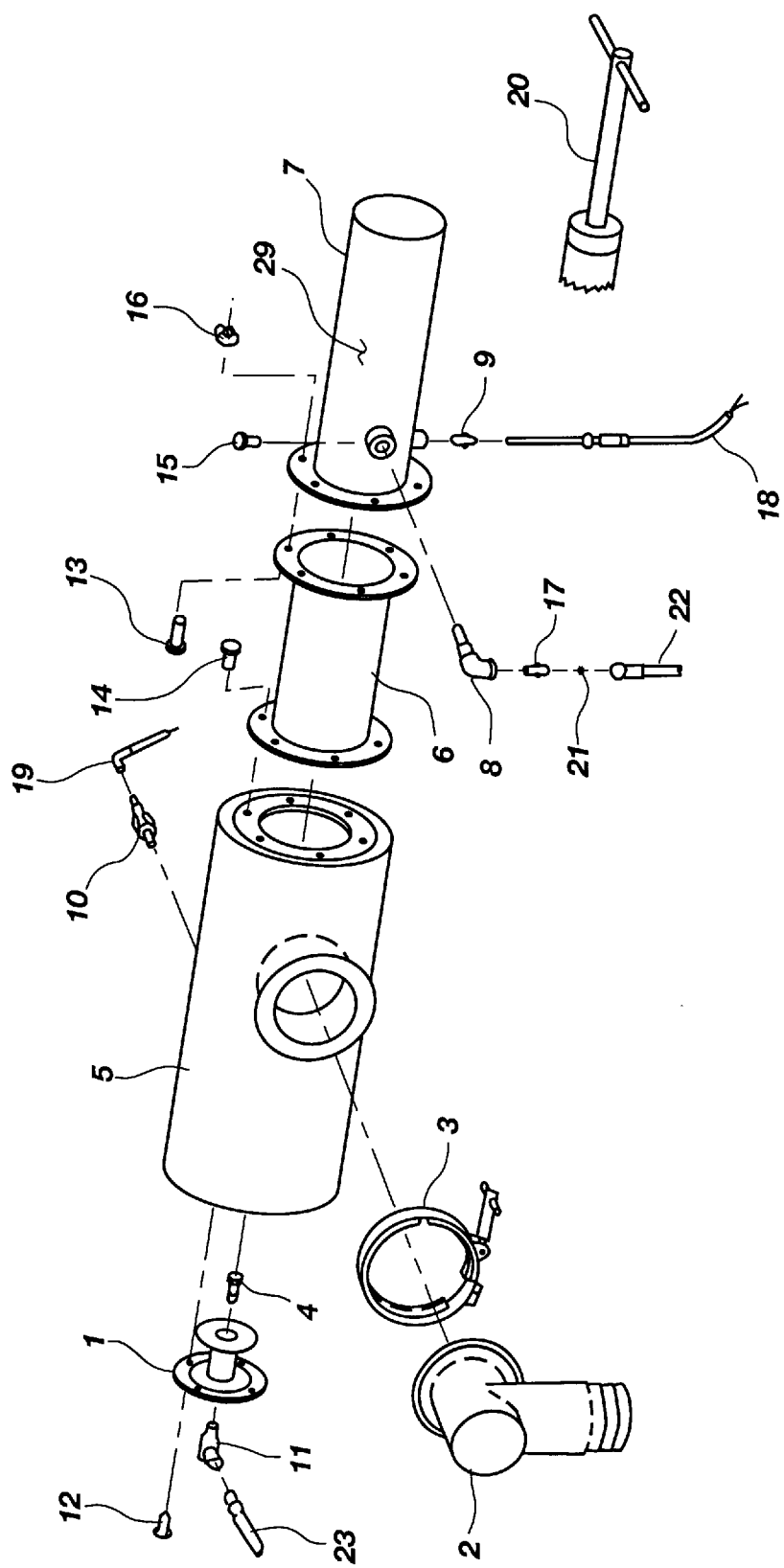
FIG. 12 is a view of a prior art device (see FIG. 4 of U.S. Pat. No. 5,935,660).

FIG. 10 is an elevational view of a stator vane assembly in which a grid-like assemblage of vanes are utilized to direct gases flowing therethrough into a turbulent pattern. FIG. 11 is a cross-sectional view along section lines 10—10 of FIG. 10.

The vanes in the center form a V-shape directing the flow of gas outwardly. The peripheral single vanes also direct gas outwardly. The vanes are positioned symmetrically about both the horizontal and vertical axes so that a sectional elevational view and a sectional plan view are visually the same.

The gases flowing through this grid-like vaned stator must change direction and are directed generally outwardly to impact the outer barrel of the aerosol generation zone and rebound to create a turbulent flow in the gas generation chamber.

What is claimed is:

1. A combustion thermal fogger having a combustion zone and an aerosol (fog) generation zone in which liquid to be fogged is introduced, wherein said combustion zone comprises:

an outer barrel and an inner barrel substantially concentric with said outer barrel to form an annular space therebetween, said inner barrel sealed to said outer barrel at its distal end and spaced from said outer barrel at its proximate end to provide communication between said annular space and an interior of said inner barrel, said outer barrel having an opening in its proximate end to accept a burner assembly;

a stator assembly having a plurality of radially positioned vanes located at the distal end of said inner barrel to separate said combustion zone from said aerosol generating zone, said vanes angled to intercept a substantially axial flow of gases created in the combustion zone, said vanes meeting at a central point and extending radially to be of substantially the same radius as the radius of the inner barrel opening at its distal end; and an air inlet means communicating with the annular space between said inner and outer barrels, said air inlet means located proximate the distal end of said inner barrel.

2. The combustion thermal fogger of claim 1, wherein said air inlet means is oriented to introduce air tangentially into said annular space.

3. The combustion thermal fogger of claim 1, wherein the distal end of said inner barrel is flared to form a hollow cone frustrum and wherein the base of said cone is sealed to an interior surface of said outer barrel.

4. The combustion thermal fogger of claim 1, wherein said stator assembly has a minimum of at least three vanes.

5. The combustion thermal fogger of claim 4, wherein each of said vanes has a substantially constant width over its entire length.

6. The combustion thermal fogger of claim 1, wherein said stator assembly has vanes positioned in a grid pattern and angled outwardly to intercept the substantially axial flow of gases created in said combustion zone to cause said gases to exit said stator assembly in a substantially turbulent manner.

7. The combustion thermal fogger of claim 1, wherein said aerosol generating zone comprises an outer cylindrical barrel sealed to the outer barrel of the combustion zone and an inner barrel concentric therewith to form an annular space therebetween and having a length shorter than said outer barrel to allow communication between the annular space and the interior of said inner barrel, said liquid to be fogged being introduced in the interior of said inner barrel of the aerosol generation zone.

8. The combustion thermal fogger of claim 1, wherein said liquid material to be fogged is introduced at a position remote from said stator assembly.

* * * * *

UNITED STATES PATENT AND TRADEMARK OFFICE
CERTIFICATE OF CORRECTION

PATENT NO. : 6,322,002 B1
DATED : November 27, 2001
INVENTOR(S) : Darol Forsythe, John Forsythe and Joel Micka It is certified that error appears in the above-identified patent and that said Letters Patent is hereby corrected as shown below:

Column 6,
Line 28, change "51b" to -- 15b --
Line 64, change "form" to -- from --

Column 7,
Line 6, "shell" to -- cylindrical pipe --
Line 10, change "shell" to -- pipe --
Line 11, change "shell" (both occurrences) to -- pipe --
Line 16, after "material" delete "25"
Line 37, change "211" to -- 21' --
Line 44, change "141" to -- 14' --

Signed and Sealed this

Eighth Day of July, 2003

JAMES E. ROGAN
*Director of the United States Patent and Trademark Office*